(12) United States Patent
Murphy, Jr. et al.

(10) Patent No.: US 10,736,928 B2
(45) Date of Patent: Aug. 11, 2020

(54) PEGYLATED RECOMBINANT BACTERIOPHAGE

(71) Applicants: Richard Brian Murphy, Jr., San Diego, CA (US); Richard Brian Murphy, San Diego, CA (US)

(72) Inventors: Richard Brian Murphy, Jr., San Diego, CA (US); Richard Brian Murphy, San Diego, CA (US)

(*) Notice: Subject to any disclaimer, the term of this patent is extended or adjusted under 35 U.S.C. 154(b) by 290 days.

(21) Appl. No.: 15/413,411

(22) Filed: Jan. 23, 2017

(65) Prior Publication Data

US 2017/0202891 A1    Jul. 20, 2017

Related U.S. Application Data

(60) Provisional application No. 62/281,178, filed on Jan. 20, 2016.

(51) Int. Cl.

| | |
|---|---|
| *A61K 35/76* | (2015.01) |
| *A61K 38/19* | (2006.01) |
| *C07K 14/52* | (2006.01) |
| *C12N 15/86* | (2006.01) |
| *A61K 47/60* | (2017.01) |
| *A61K 38/00* | (2006.01) |

(52) U.S. Cl.
CPC ......... *A61K 35/76* (2013.01); *A61K 38/195* (2013.01); *A61K 47/60* (2017.08); *C07K 14/521* (2013.01); *C07K 14/523* (2013.01); *C12N 15/86* (2013.01); *A61K 38/00* (2013.01); *C12N 2795/00032* (2013.01); *C12N 2795/00043* (2013.01)

(58) Field of Classification Search
None
See application file for complete search history.

(56) References Cited

U.S. PATENT DOCUMENTS

| | | | |
|---|---|---|---|
| 4,593,002 A | 6/1986 | Dulbecco | |
| 6,649,158 B1 | 11/2003 | LaFace | |
| 7,332,307 B2 | 1/2008 | Carlton et al. | |
| 2004/0161431 A1* | 8/2004 | Carlton | C12N 7/00 424/184.1 |
| 2011/0039761 A1* | 2/2011 | Eckert | A61K 8/64 514/2.4 |

FOREIGN PATENT DOCUMENTS

EP       2179035 B1    2/2013

OTHER PUBLICATIONS

Samson et al., 2013, Nat. Rev. Microb. 11:675-687 (Year: 2013).*
Iandolo, et al (2002) Gene 289:109-118, Comparative analysis of the genomes of the tempaerate bacteriphages phi-11, phi-12, and phi13 of *Staphyococcus aureus* 8325.
McAuliffe (May 2011); Anti-MRSA—phage therapy alternatives for controlling MRSA; Agrigulture and Food Development Authority Technology Updates; http:www/teagasc.ie/publications; Downloaded Jan. 19, 2016.
Merril, et al (1996) PNAS(USA) 93:3188-3192, "Long-curculating bacteriophage as antibacterial agents".
Soto, et al (1998) PNAS(SA) 95:8205-8210, "The CC chemokine 6Ckine binds the CSC chemokine receptor CSCR3".
Jassim and Limoges (2014) World Journal Microbiol Biotech 30:2153-2170, "Natural solution to antibiotic resistance: bacteriophages 'The Living Drugs'".
Morales, et al (1999) PNAS USA 96(25):14470-14475, "CTACK, a skin-associated chemokine that preferentially attracts skin-homing memory T cells".
Shim and Kwon (2010) The FEBS Journal 277:4814-4827, "Efficient and targeted delivery of siRNA in vivo".
Dorner, et al (2002) PNAS 99(9)6181-6186, "MIP-1 , MIP-1 , RANTES, and ATAC lymphotactin function together with IFN—as type 1 cytokines".
Hultmark, et al (1980) Eur. J. Biochem. 106:7-16, "Insect Immunity. Purification and Properties of Three Inducible Bactericidal Proteins from Hemolymph of Immunized Pupae of Hyalophora cecropia".
Smith and Gingrich (2005) Biotechniques 39:879-884, "Hydroxyapatite chromatography of phage-display virions".
Kaur, et al (2012) Journal of Nano technology Article ID 247427, "Immunocompatibility of Bacteriophages as Nanomedicines".
Maruyama, et al (1994) PNAS(USA) 91:8273-8277, "[Lambda]foo:A A [lambda]phage vector for the expression of foreign proteins".
Hromas, et al (1997) Blood 89:3315-3322, "Cloning and Characterization of Exodus, a Novel b-Chemokine".

(Continued)

*Primary Examiner* — James D Schultz

(57) ABSTRACT

The present invention provides a recombinantly modified PEGylated bacteriophage expressing a mammalian antigen presenting cell chemoattractant. The present invention further provides methods of treatment of mammalian subjects having a bacterial infection by the administration of a pharmaceutically acceptable formulation of a recombinantly modified PEGylated bacteriophage expressing a mammalian antigen presenting cell chemoattractant. The present invention further provides pharmaceutically acceptable formulations of recombinantly modified PEGylated bacteriophage expressing a mammalian antigen presenting cell chemoattractant. The present invention further provides a method of inducing an antibacterial immune response in a mammalian subject having bacterial infection by the administration of a pharmaceutically acceptable formulation of a recombinantly modified PEGylated bacteriophage expressing a mammalian antigen presenting cell chemoattractant. The present invention further provides a recombinantly modified PEGylated bacteriophage that avoids neutralization by the Cas9 system. In one embodiment, the present invention further provides a recombinantly modified PEGylated bacteriophage expressing an anti-Cas9 protein. The present invention further provides a recombinantly modified PEGylated bacteriophage the genome of which has been modified to eliminate one or more protospacer adjacent motifs.

9 Claims, No Drawings

(56) References Cited

OTHER PUBLICATIONS

Seow and Wood (2009) Molecular Therapy 17:767-777, "Biological Gene Delivery Vehicles: Beyond Viral Vectors".
Lu and Koeris (2011) Current Opinion in Microbiology 12:1-8, "The next generation of bacteriophage therapy".
Kim, et al (2008) 1(3):247-257, "PEGylation of bacteriophages increases blood circulation time and reduces T-helper type 1 immune response".
Kling (2013) BioProcess International 11(3):35-43, "PEGylation of Biologics: A Multipurpose Solution".
Xia and Wolz (2014) Infection, Genetics and Evolution 21:593-601, "Phages of Staphylococcus aureus and their Impact on host evolution".
Keen (2012) Frontiers in Microbiology vol. 3 Article 238, pp. 1-3, "Phage therapy: concept to cure".
Thomas, et al (1974) PNAS(USA) 71(11):4579-4583, "Viable Molecular Hybrids of Bacteriophage Lambda and Eukaryotic DNA".
Zakharova, et al (2005) BioTechniques 38:194-198, "Purification of filamentous bacteriophage for phage display using size-exclusion chromatography".
Thomason, et al. (2009) Bacteriophages: Methods an Protocols, vol. 1 Isolation Characterization and Interactions, Chapter 21: Modifying Bacteriophage [lambda] with Recombineering.
Udekwu KI, Levin BR (2012) *Staphylococcus aureus* in Continuous Culture: A Tool for the Rational Design of Antibiotic Treatment Protocols. PLoS One 7(7): e38866. doi:10.1371/journal.pone.0038866.
Estrem, et al (1998) PNAS(USA) 95:9761-9766, "Identification of an UP element consensus sequence for bacterial promoters".
Deghorain and Van Melderen (2012) Viruses 4:3316-3335, "The *Staphylococci phages* Family: An Overview".
Stone, R. (2002) Science 298:728-731, "Stalin's Forgotten Cure".
Graves, et al (2010) J Mol Med (Berl) 88(2): 109-114, "Community-associated methicillin-resistant *Staphylococcus aureus* immune evasion and virulence".

\* cited by examiner

PEGYLATED RECOMBINANT BACTERIOPHAGE

CROSS REFERENCE TO OTHER APPLICATIONS

The present application is related to and claims the priority pursuant to 35 U.S.C. § 119 of U.S. Provisional Patent Application Ser. No. 62/281,178 filed Jan. 20, 2016.

BACKGROUND OF THE INVENTION

Bacteriophage (or "phage") are viruses that infect bacterial cells. Bacteriophage were first identified in the early 20$^{th}$ century and their property of being able infect and destroy bacterial cells was widely employed in a therapeutic context for the treatment of bacterial infections with significant effect. However, the lack of well controlled studies regarding the application of phage therapy in the 1930s and 1940s led significant to issues regarding proper dosage and treatment regimens. The reported utility of phage therapy varied widely in the literature. The lack of controlled studies for the use of phage therapy combined with the advent of small molecule antibiotics in the 1940s led to a decline in the reliance on phage therapy for the treatment of bacterial infections. Continuing improvements in small molecule antibiotic compounds led to their near universal adoption in the clinic as the standard of care for the treatment of bacterial infections. As a result, the necessary well controlled clinical studies to standardize phage therapy were not conducted and phage therapy widely fell into disrepute. However, the growing acceptance of biological therapies such as engineered viruses and modified cellular therapies has resulted in many investigators revisiting the use of phage in the treatment of bacterial infections, particularly those that are resistant to small molecule therapies such as MRSA and a reassessment of their safety. Several clinical investigations have been initiated to evaluate the use of bacteriophage in the clinic. For example, the PHAGOBURN study (ClinicalTrials.gov Identifier: NCT02116010), a EU Framework 7 funded program is investigating the use of cocktails of *E. coli* phages and *Pseudomonas aeruginosa* in the treatment of burn victims Since 2006, the United States Food and Drug Administration has approved the use of bacteriophages for the selective elimination of bacteria in foods such as *Listeria monocytogenes* (Listex, Micreos Food Safety BV, Wageningen, The Netherlands) and a variety of *Salmonella* species (SalmoFresh, IntraLytix, Inc., Baltimore, Md.), the latter being approved in 2013 as a GRAS food additive.

One hurdle to the use of bacteriophage for the treatment of systemic infections in mammals is that the phage particle is immunogenic resulting in neutralization by the mammalian immune system, particularly upon repeat administration. The immune response to systemic administration of phage results in significant variation in efficacy, circulating half-life of the phage agent and significantly limits the possibility of repeated administration of phage therapies. The administration of immunosuppressant compounds to a subject suffering from an infectious disease to avoid clearance of the bacteriophage is not clinically acceptable. Consequently, efforts have been made to mask the immunogenic character of the phage particle.

The conjugation of polyethylene glycol polymers ("PEGylation") to biological agents to avoid immune clearance and prolong circulating half-life is well known in the art. A variety of PEGylated biological agents have been approved by regulatory authorities and are routinely used by clinicians for the treatment of a variety of diseases. Based on this experience, the PEGylation of bacteriophage has been proposed for the systemic treatment of bacterial infections. See e.g., Carlton, et al. U.S. Pat. No. 7,332,307 B2 issued Feb. 19, 2008. However, the prolonging the half-life of the phage and shielding it from immune surveillance does not provide durable protection from future infection by bacteria. In particular, some particularly lethal strains of *S. aureus* (typically referred to as methicillin resistant or multidrug resistant *Staphylococcus aureus* or MRSA) have demonstrated complex systems to avoid immune surveillance as well as the ability to rapidly adapt resistance to therapeutic agents. MRSA arose primarily through the widespread use of broad spectrum antibiotics. Consequently, the design of an agent that attacks and kills a particular strain of MRSA will likely have limited future effect as the bacteria has evolved the ability to rapidly mutate to avoid such agents.

Consequently, there is a need in the art for an antibacterial agent that enables both systemic administration and the ability to recruit and train the immune system to recognize and attack dispersed and/or recurrent infections. The present invention addresses this need.

SUMMARY OF THE INVENTION

The present invention provides a recombinantly modified PEGylated bacteriophage expressing a mammalian antigen presenting cell chemoattractant. The present invention further provides methods of treatment of mammalian subjects having a bacterial infection by the administration of a pharmaceutically acceptable formulation of a recombinantly modified PEGylated bacteriophage expressing a mammalian antigen presenting cell chemoattractant. The present invention further provides pharmaceutically acceptable formulations of recombinantly modified PEGylated bacteriophage expressing a mammalian antigen presenting cell chemoattractant. The present invention further provides a method of inducing an antibacterial immune response in a mammalian subject having bacterial infection by the administration of a pharmaceutically acceptable formulation of a recombinantly modified PEGylated bacteriophage expressing a mammalian antigen presenting cell chemoattractant. The present invention further provides a recombinantly modified PEGylated bacteriophage that avoids neutralization by the Cas9 system. In one embodiment, the present invention further provides a recombinantly modified PEGylated bacteriophage expressing an anti-Cas9 protein. The present invention further provides a recombinantly modified PEGylated bacteriophage the genome of which has been modified to eliminate one or more protospacer adjacent motifs.

DETAILED DESCRIPTION OF THE INVENTION

Detailed embodiments of the present invention are disclosed herein. However, it is to be understood that the disclosed embodiments are merely illustrative of the invention that may be embodied in various forms. In addition, each of the examples given in connection with the various embodiments of the invention are intended to be illustrative, and not restrictive. Specific structural and functional details disclosed herein are not to be interpreted as limiting, but merely as a representative basis for teaching one skilled in the art to variously employ the present invention. Furthermore, any section headings are merely for convenience of the reader and not intended to provide a limitation on the scope of the disclosure with respect to any feature of utility of the present invention.

The present invention provides a recombinantly modified PEGylated bacteriophage, said PEGylated bacteriophage capable of infecting a bacterial cell, the genome of said bacteriophage comprising an expression cassette comprising a promoter active in said bacterial cell capable operably linked to a nucleic acid sequence encoding an mAPCC polypeptide, said expression cassette inserted into a non-essential region of a bacteriophage genome, such that infection of a bacterial cell by said recombinantly modified bacteriophage results in the expression of said mAPCC polypeptide in said infected bacterial cell. In one embodiment, the bacteriophage is a lytic phage such that the bacteriophage induces the lytic pathway of the bacterial cell following infection resulting local release of the mAPCC from the site of infection. In one embodiment, the mAPCC polypeptide is selected from the group consisting of fMLP, MCP-1, MCP-2, MCP-3, MIP-1α/LD78, MIP-1β, MIP-3α, MIP-3β, 6-CKINE, lymphotactin and RANTES.

The present invention further provides a recombinantly modified PEGylated bacteriophage, said PEGylated bacteriophage capable of infecting a bacterial cell, the genome of said bacteriophage comprising an expression cassette comprising a promoter active in said bacterial cell capable operably linked to a nucleic acid sequence encoding an anti-Cas9 protein, said expression cassette inserted into a non-essential region of a bacteriophage genome, such that infection of a bacterial cell by said recombinantly modified bacteriophage results in the expression of said anti-Cas9 protein polypeptide in said infected bacterial cell.

The present invention further provides a recombinantly modified PEGylated bacteriophage, said PEGylated bacteriophage capable of infecting a bacterial cell, the genome of said bacteriophage comprising elimination of one or more or more protospacer adjacent motifs.

The present invention further provides a recombinantly modified PEGylated bacteriophage, said PEGylated bacteriophage capable of infecting a bacterial cell, the genome of said bacteriophage comprising an expression cassette comprising a promoter active in said bacterial cell capable operably linked to a nucleic acid sequence encoding an anti-Cas9 protein and an expression cassette comprising a promoter active in said bacterial cell capable operably linked to a nucleic acid sequence encoding an mAPCC polypeptide, said expression cassettes inserted into a non-essential region of a bacteriophage genome, such that infection of a bacterial cell by said recombinantly modified bacteriophage results in the expression of said mAPCC polypeptide and said anti-Cas9 protein polypeptide in said infected bacterial cell.

The present invention further provides a recombinantly modified PEGylated bacteriophage, said PEGylated bacteriophage capable of infecting a bacterial cell, the genome of said bacteriophage comprising an expression cassette comprising a promoter active in said bacterial cell capable operably linked to a nucleic acid sequence encoding an anti-Cas9 protein and an expression cassette comprising a promoter active in said bacterial cell capable operably linked to a nucleic acid sequence encoding an mAPCC polypeptide, said expression cassettes inserted into a non-essential region of a bacteriophage genome, such that infection of a bacterial cell by said recombinantly modified bacteriophage results in the expression of said mAPCC polypeptide and said anti-Cas9 protein polypeptide in said infected bacterial cell, said genome of said bacteriophage comprising being modified to eliminate one or more or more protospacer adjacent motifs.

The present invention further provides a method of inducing lysis of a bacterial cell and expression a mAPCC molecule in said bacterial cell by contacting said bacterial cell with a recombinantly modified PEGylated lytic bacteriophage, said PEGylated bacteriophage capable of infecting and inducing the lytic pathway of said bacterial cell, the genome of said bacteriophage comprising an expression cassette comprising a promoter active in said bacterial cell capable operably linked to a nucleic acid sequence encoding an mAPCC polypeptide, said expression cassette inserted into a non-essential region of said bacteriophage genome, such that infection of a bacterial cell by said recombinantly modified bacteriophage results in the expression of said mAPCC polypeptide in said infected bacterial cell and lysis of said bacterial cell. APCs are recruited to the site of infection in response to the expressed mAPCC where they integrate and present bacterial antigens. This is particularly relevant where the intact bacterial cell has evolved complex mechanisms to avoid immune surveillance by the host (e.g. MRSA).

The present invention further provides a method of inducing lysis of a bacterial cell by contacting said bacterial cell with a recombinantly modified PEGylated bacteriophage, said PEGylated bacteriophage capable of infecting a bacterial cell, the genome of said bacteriophage comprising an expression cassette comprising a promoter active in said bacterial cell capable operably linked to a nucleic acid sequence encoding an anti-Cas9 protein, said expression cassette inserted into a non-essential region of a bacteriophage genome, such that infection of a bacterial cell by said recombinantly modified bacteriophage results in the expression of said anti-Cas9 protein polypeptide in said infected bacterial cell.

The present invention further provides a method of inducing lysis of a bacterial cell by contacting said bacterial cell with a recombinantly modified PEGylated bacteriophage, said PEGylated bacteriophage capable of infecting a bacterial cell, the genome of said bacteriophage comprising modifications to the phage genome to eliminate one or more or more protospacer adjacent motifs.

The present invention further provides a method of inducing lysis of a bacterial cell by contacting said bacterial cell with a recombinantly modified PEGylated bacteriophage, said PEGylated bacteriophage capable of infecting a bacterial cell, the genome of said bacteriophage comprising an expression cassette comprising a promoter active in said bacterial cell capable operably linked to a nucleic acid sequence encoding an anti-Cas9 protein and an expression cassette comprising a promoter active in said bacterial cell capable operably linked to a nucleic acid sequence encoding an mAPCC polypeptide, said expression cassettes inserted into a non-essential region of a bacteriophage genome, such that infection of a bacterial cell by said recombinantly modified bacteriophage results in the expression of said mAPCC polypeptide and said anti-Cas9 protein polypeptide in said infected bacterial cell.

The present invention further provides a method of inducing lysis of a bacterial cell by contacting said bacterial cell with a recombinantly modified PEGylated bacteriophage, said PEGylated bacteriophage capable of infecting a bacterial cell, the genome of said bacteriophage comprising an expression cassette comprising a promoter active in said bacterial cell capable operably linked to a nucleic acid sequence encoding an anti-Cas9 protein and an expression cassette comprising a promoter active in said bacterial cell capable operably linked to a nucleic acid sequence encoding an mAPCC polypeptide, said expression cassettes inserted into a non-essential region of a bacteriophage genome, such that infection of a bacterial cell by said recombinantly modified bacteriophage results in the expression of said mAPCC polypeptide and said anti-Cas9 protein polypeptide in said infected bacterial cell, said genome of said bacteriophage comprising being modified to eliminate one or more or more protospacer adjacent motifs.

The present invention further provides a method of treating a mammalian subjects having a bacterial infection by the administration of a pharmaceutically acceptable formulation of a recombinantly modified PEGylated bacteriophage, said PEGylated bacteriophage capable of infecting a bacterial cell, the genome of said bacteriophage comprising an expression cassette comprising a promoter active in said bacterial cell capable operably linked to a nucleic acid sequence encoding an mAPCC polypeptide, said expression cassette inserted into a non-essential region of said bacteriophage genome, such that infection of a bacterial cell by said recombinantly modified bacteriophage results in the expression of said mAPCC polypeptide in said infected bacterial cell. In one embodiment of the method of the present invention, the bacteriophage is administered at a dosage of from $1 \times 10^9$ to about $1 \times 10^{13}$ pfu/kg of bodyweight.

The present invention further provides a method of treating a mammalian subjects having a bacterial infection by the administration of a pharmaceutically acceptable formulation of a recombinantly modified PEGylated bacteriophage, said PEGylated bacteriophage capable of infecting a bacterial cell, the genome of said bacteriophage comprising an expression cassette comprising a promoter active in said bacterial cell capable operably linked to a nucleic acid sequence encoding an anti-Cas9 protein, said expression cassette inserted into a non-essential region of a bacteriophage genome, such that infection of a bacterial cell by said recombinantly modified bacteriophage results in the expression of said anti-Cas9 protein polypeptide in said infected bacterial cell.

The present invention further provides a method of treating a mammalian subjects having a bacterial infection by the administration of a pharmaceutically acceptable formulation of a recombinantly modified PEGylated bacteriophage, said PEGylated bacteriophage capable of infecting a bacterial cell, the genome of said bacteriophage comprising modifications to eliminate one or more or more protospacer adjacent motifs.

The present invention further provides a method of treating a mammalian subjects having a bacterial infection by the administration of a pharmaceutically acceptable formulation of a recombinantly modified PEGylated bacteriophage, said PEGylated bacteriophage capable of infecting a bacterial cell, the genome of said bacteriophage comprising an expression cassette comprising a promoter active in said bacterial cell capable operably linked to a nucleic acid sequence encoding an anti-Cas9 protein and an expression cassette comprising a promoter active in said bacterial cell capable operably linked to a nucleic acid sequence encoding an mAPCC polypeptide, said expression cassettes inserted into a non-essential region of a bacteriophage genome, such that infection of a bacterial cell by said recombinantly modified bacteriophage results in the expression of said mAPCC polypeptide and said anti-Cas9 protein polypeptide in said infected bacterial cell.

The present invention further provides a method of treating a mammalian subjects having a bacterial infection by the administration of a pharmaceutically acceptable formulation of a recombinantly modified PEGylated bacteriophage, said PEGylated bacteriophage capable of infecting a bacterial cell, the genome of said bacteriophage comprising an expression cassette comprising a promoter active in said bacterial cell capable operably linked to a nucleic acid sequence encoding an anti-Cas9 protein and an expression cassette comprising a promoter active in said bacterial cell capable operably linked to a nucleic acid sequence encoding an mAPCC polypeptide, said expression cassettes inserted into a non-essential region of a bacteriophage genome, such that infection of a bacterial cell by said recombinantly modified bacteriophage results in the expression of said mAPCC polypeptide and said anti-Cas9 protein polypeptide in said infected bacterial cell, said genome of said bacteriophage comprising modifications eliminate one or more or more protospacer adjacent motifs.

The present invention further provides pharmaceutically acceptable formulation of a recombinantly modified PEGylated bacteriophage, said PEGylated bacteriophage capable of infecting a bacterial cell, the genome of said bacteriophage comprising an expression cassette comprising a promoter active in said bacterial cell capable operably linked to a nucleic acid sequence encoding an mAPCC polypeptide, said expression cassette inserted into a non-essential region of said bacteriophage genome, such that infection of a bacterial cell by said recombinantly modified bacteriophage results in the expression of said mAPCC polypeptide in said infected bacterial cell.

The present invention further provides pharmaceutically acceptable formulation of a recombinantly modified PEGylated bacteriophage, said PEGylated bacteriophage capable of infecting a bacterial cell, the genome of said bacteriophage comprising an expression cassette comprising a promoter active in said bacterial cell capable operably linked to a nucleic acid sequence encoding an anti-Cas9 protein, said expression cassette inserted into a non-essential region of a bacteriophage genome, such that infection of a bacterial cell by said recombinantly modified bacteriophage results in the expression of said anti-Cas9 protein polypeptide in said infected bacterial cell.

The present invention further provides pharmaceutically acceptable formulation of a recombinantly modified PEGylated bacteriophage, said PEGylated bacteriophage capable of infecting a bacterial cell, the genome of said bacteriophage comprising elimination of one or more or more protospacer adjacent motifs.

The present invention further provides pharmaceutically acceptable formulation of a recombinantly modified PEGylated bacteriophage, said PEGylated bacteriophage capable of infecting a bacterial cell, the genome of said bacteriophage comprising an expression cassette comprising a promoter active in said bacterial cell capable operably linked to a nucleic acid sequence encoding an anti-Cas9 protein and an expression cassette comprising a promoter active in said bacterial cell capable operably linked to a nucleic acid sequence encoding an mAPCC polypeptide, said expression cassettes inserted into a non-essential region of a bacteriophage genome, such that infection of a bacterial cell by said recombinantly modified bacteriophage results in the expression of said mAPCC polypeptide and said anti-Cas9 protein polypeptide in said infected bacterial cell.

The present invention further provides pharmaceutically acceptable formulation of a recombinantly modified PEGylated bacteriophage, said PEGylated bacteriophage capable of infecting a bacterial cell, the genome of said bacteriophage comprising an expression cassette comprising a promoter active in said bacterial cell capable operably linked to a nucleic acid sequence encoding an anti-Cas9 protein and an expression cassette comprising a promoter active in said bacterial cell capable operably linked to a nucleic acid sequence encoding an mAPCC polypeptide, said expression cassettes inserted into a non-essential region of a bacteriophage genome, such that infection of a bacterial cell by said recombinantly modified bacteriophage results in the expression of said mAPCC polypeptide and said anti-Cas9 protein polypeptide in said infected bacterial cell, said genome of said bacteriophage comprising being modified to eliminate one or more or more protospacer adjacent motifs.

The present invention further provides a method of inducing a durable immune response in a mammalian subject infected with a bacteria against future infection by said bacteria by the administration of a recombinantly modified PEGylated lytic bacteriophage, said PEGylated bacteriophage capable of infecting and inducing the lytic pathway of said bacterial cell, the genome of said bacteriophage comprising an expression cassette comprising a promoter active in said bacterial cell capable operably linked to a nucleic acid sequence encoding an mAPCC polypeptide, said expression cassette inserted into a non-essential region of said bacteriophage genome, such that infection of a bacterial cell by said recombinantly modified bacteriophage results in the expression of said mAPCC polypeptide in said infected bacterial cell and lysis of said bacterial cell releasing said mAPCC from said transfected bacterial cell.

Bacteriophage

As used herein, the term "bacteriophage" is used interchangeably with the term "phage" to describe any of a variety of bacterial viruses that infect and replicate within a bacterium. A wide variety of bacteriophages capable of selection a broad range of bacterial cells have been identified and characterized extensively in the scientific literature. Since bacteriophages exhibit significant selectivity in the bacterial cell susceptible to infection, the bacteriophage is typically selected in view of the target bacterium responsible for the infection in the host. Samples of bacteriophages suitable as starting material for the generation of the recombinantly engineered bacteriophage against any of a wide variety of bacterial cells are available from the American Type Culture Collection (Manassas, Va.). The manipulation of the phage genome is conducted in accordance with standard methodologies for the manipulation of recombinant nucleic acids well known to those of skill in the art such as those describing in Molecular Cloning: A Laboratory Manual (available from Cold Spring Harbor Press) and conventional reagents available from a wide variety of laboratory supply houses.

Mammalian Antigen Presenting Cell Chemoattractant:

As used herein, the term "chemoattractant" is used to describe a molecule that exerts positive chemotaxis, i.e. attraction of cells to the location of the chemoattractant. An antigen presenting cell chemoattractant ("APCC") is a molecule that exerts positive chemotaxis of antigen presenting cells (APCs). A mammalian APCC ("mAPCC") is a polypeptide active in a mammalian subject that exerts positive chemotaxis of antigen presenting cells.

The term "antigen presenting cells" or "APCs" is used to refer to mammalian immunocompetent cells that mediate the cellular immune response by processing and presenting antigens to the T-cells. APCs include macrophages, dendritic cells, Langerhans cells and B-lymphocytes. In one embodiment, the APC is a dendritic cell, especially an immature dendritic cell. Dendritic cells are professional antigen presenting cells. Immature dendritic cells exhibit a phenotype in which most class II molecules are intracellular and localized to lysosomes and in this phase are capable of uptake of foreign antigens. Immature dendritic cells "patrol" the peripheral tissues in search of foreign antigens. Following antigen uptake, immature dendritic cells mature into an intermediate phenotype in which intracellular class II molecules are found in peripheral non-lysosomal vesicles followed by maturation into late dendritic cells which express almost all of their class II molecules on the plasma membrane. The maturing dendritic cells migrate to the lymph nodes where they present the processed peptides to T-cells. Bacteriophage vectors are particularly suited for the in vivo as delivery and expression of mAPCCs. The administration of a recombinant PEGylated bacteriophage expressing a mAPCC provides in vivo stimulation of dendritic cells to stimulate dendritic cell mediated immunotherapy in vivo.

The compositions of the present invention may be administered as a monotherapy or alternatively in combination with genetic adjuvants such as cytokines, to mobilize dendritic cells and induce differentiation and activation, as well as chemokines to direct immature dendritic cells to the infection site and mature dendritic cells to the lymph nodes. Examples of such genetic adjuvants include but are not limited to IL-4, GM-CSF, CD40 ligand, TNF-alpha or LPS. The compositions of the present invention effectively induce inflammatory responses mediated by APCs at the site of infection to enable the immune response to overcome the natural tolerance mechanisms employed by bacterial cells to evade immune surveillance.

Examples of mAPCCs useful in the practice of the present invention include but are not limited to the chemokines fMLP (representative of formyl peptides of bacterial origin), C5a and the C—C chemokines monocyte chemotactic protein (MCP)-1, MCP-2, MCP-3, macrophage inflammatory protein (MIP)-1α/LD78, MIP-1β, MIP-3α, MIP-3β, 6-CKINE, lymphotactin and RANTES, have been involved in the recruitment and chemotactic migration of dendritic cells. These chemokines have been demonstrated to induce positive chemotaxis of APCs. Sozzani, et al. (1995) J. Immunol. 1995 155(7):3292-5, Xu, et al. (1996) J. Leukoc. Biol. 60(3):365-71. Greaves, et al. (1997) J. Exp. Med. 186(6): 837-44. The mAPCC may be expressed in and intracellular form where it is released upon cell lysis or in secreted form by the use of a signal peptide. In the preferred practice of the invention, the mAPCC is selected from the group consisting of MIP-3-α, macrophage inflammatory protein (MIP)-1α/LD78, and/or MW 3β to induce migration to the lymph nodes. In the most preferred practice of the invention, the mAPCC is MIP-3-α.

Engineering of Phage to Encode and Express the mAPCC in a Target Cell

The delivery of the mAPCC polypeptide to the site of infection is achieved by a bacteriophage capable of infecting the target cell, said bacteriophage modified using recombinant technology to introduce an expression cassette comprising a promoter active in the target bacterial cell capable operably linked to a nucleic acid sequence encoding an mAPCC polypeptide, said expression cassette inserted into a non-essential region of a bacteriophage genome such that following transfection of the target bacterial cell by the recombinantly engineered bacteriophage, the mAPCC polypeptide is expressed in the target bacterial cell. For example, in the case of bacteriophage targeting *S. aureus* cells, the expression cassette would employ a *S. aureus* promoter driving expression of the MICC inserted into a non-essential region of the *S. aureus* specific bacteriophage. The identification of non-essential regions of the bacteriophage genome are readily identified by the known genomic organization and coding sequences of such phages.

Bacteriophages are typically exhibit selective infectivity for a given strain of bacteria and are typically categorize with respect to their target cells. For example, *E. coli* bacteriophage exhibit highly preferential infectivity for *E. coli* cells, *S. aureus* bacteriophage exhibit highly preferential infectivity for *S. aureus* strains, and so forth.

The term "transfected" or "transformed" or "transduced" are used interchangeably herein to refer to a process by which exogenous nucleic acid is transferred or introduced into the host cell. A transfected, transformed, or transduced cell is one which has been transfected, transformed or transduced with exogenous nucleic acid and the term includes the transfected, transformed, or transduced cell's progeny. The term "recombinant" as used herein refers to nucleic sequences constructed by methods of recombinant DNA technology, also termed "genetic engineering".

The term "expression cassette" refers to a recombinant (or synthetic) nucleic acid construct that encodes a desired polypeptide operably linked to suitable genetic control elements that are capable of effecting expression of the polypeptide in the target cell to be transformed with the engineered bacteriophage. In one embodiment, the genetic control element is a promoter. The term "promoter" is used in its conventional sense to refer to a nucleotide sequence at which the initiation and rate of transcription of a coding sequence is controlled. The promoter contains the site at which RNA polymerase binds and also contains sites for the binding of regulatory factors (such as repressors or transcription factors). Promoters can be naturally occurring or synthetic. A promoter is operably linked to a coding sequence if it controls the transcription of the polypeptide; a ribosome binding site is operably linked to a coding sequence if it is positioned to permit translation. The promoter may be constitutively active, inducible or temporally regulated. Inducible promoters are activated in response to factors in the environment of the promoter such as the presence of a chemical agent or physical conditions of the environment such as temperature. The term "temporal promoters" refers to promoters which drive transcription or the mAPCC coding sequence at a point later in the phage infectious cycle.

Prokaryotic promoter sequences promoter sequences active in a wide variety of bacteria are well known in the art. Promoter sequences may be obtained from excising naturally occurring sequences or through sequencing and synthetic synthesis of nucleic acid sequences corresponding to naturally occurring prokaryotic promoter sequences of the target bacterial cell. Typical prokaryotic promoter sequences comprise two short sequence elements at positions approximately −10 and −35 nucleotides upstream from the transcription start site. The sequence at the −10 position typical comprises the consensus sequence TATAAT. The sequence at −35 position typically comprises the consensus sequence TTGACA. However, although the above consensus sequences are conserved on average, these particular sequences are not found intact in most bacterial promoters. The optimal spacing between the −35 and −10 sequences is approximately 17 base pairs. See, e.g. Estrem, et al. (1999) *Bacterial promoter architecture: Subsite structure of UP elements and interactions with the carboxy-terminal domain of the RNA polymerase alpha subunit*; Genes & Development 13(16): 2134-2147.

As used herein, a nucleic acid sequence which "encodes" a particular polypeptide is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. The term "operably linked" refers to a linkage of polynucleotide elements in a functional relationship. A nucleic acid sequence is "operably linked" when it is placed into a functional relationship with another nucleic acid sequence. Typically, nucleotide sequences that are operably linked are contiguous.

The amino acid sequences and corresponding encoding nucleic acid sequences if mAPCCs are known in the art. In one embodiment of the invention, the mammalian sequence of the mAPCCs is optimized for expression in the bacterial cell target environment through the use of codons optimized for expression. The techniques for the construction of synthetic nucleic acid sequences encoding mAPCCs using and preferred codons optimal for bacterial cell expression may be determined by computational methods analyzing the commonality of codon usage for encoding native proteins of the bacteriophage genome and their relative abundance by techniques well known in the art. The codon usage database (http://www.kazusa.or.jp/codon) may be used for generation of codon optimized sequences in bacterial environments. Furthermore, a variety of software tools are available to convert sequences from one organism to the optimal codon usage for a different host organism such as the JCat Codon Optimization Tool (www.jcat.de), Integrated DNA technologies Codon Optimization Tool (https://www.idtdna.com/CodonOpt) or the Optimizer online codon optimization tool (http://genomes.urv.es/OPTIMIZER). Such synthetic sequences may be constructed by techniques well known in the art for the construction of synthetic nucleic acid molecules and may be obtained from a variety of commercial vendors.

The bacteriophage genome may be modified to incorporate multiple expression cassettes to enable the targeted expression of multiple mAPCCs and/or other polypeptide agents as described herein which may be co-administered with the compositions of the present invention such as additional cytokines, chemokines or APC maturation factors.

The bacteriophage genome may be modified to incorporate additional genes, such as those encoding drug resistance, can be included to allow selection or screening for the presence of the recombinant phage. Such additional genes can include, for example, genes encoding neomycin resistance, ampicillin resistance, kanamycin resistance, thymidine kinase, beta-galactosidase, dihydrofolate reductase (DHFR), and chloramphenicol acetyl transferase.

Co-expression of multiple proteins from the bacteriophage of the present invention in the bacterial environment can be achieved by multiple monocistronic expression, polycistronic expression based on the RBS (Karamitros and Konrad (2014) Protein Expression and Purification 93:1-10), or the dual-intein (DI) domain (as described in Zhang, et al. (2015) Scientific Reports 5:8541, DOI 10.1038) technologies.

Avoiding Bacterial Host Neutralization

In addition to, or in the alternative to, the expression of an mAPCC polypeptide, the PEGylated recombinant bacteriophage of the present invention may be modified to avoid or inhibit the defense mechanisms of the bacterial host cell. Bacterial hosts have developed defense mechanisms to guard against bacteriophage infection. A primary example of such a bacterial host defense system is Cas9 endonuclease which introduces a double strand DNA cleavage inactivating the phage. Cas9 is a protein linked to a crRNA sequence that is homologous to phage sequences. The Cas9 endonuclease surveys the genome to identify a protospacer adjacent motif (PAM) site which is essential for Cas9 to bind to the target DNA. The PAM sequences from a variety of variety of organisms have been identified are primarily based on the 5'-NGG-3' prototypical sequence, where N is any nucleotide and G is guanidine. As PAM sequences are essential for Cas9 function, elimination of Cas9 sequences from phage minimizes the ability of the Cas9 endonuclease from neutralizing the invading phage.

In one embodiment of the invention, the phage is modified to eliminate one or more PAM sites. Evaluation of the phage genome to identify PAM sequences can be achieved by automated sequencing techniques. The effective elimination of PAM sequences (e.g., TGG, AGG, CGG and GGG) can be achieved by site directed mutagenesis techniques well known in the art. In some instances, the PAM sequence may be located within a sequence of the phage genome that encodes a protein. In such instances, elimination of the PAM site has the potential to give rise to a point mutation in the coding sequence resulting in an amino acid substitution. In such instances, it is preferred to modify the PAM sequence to introduce a conservative amino acid substitution in the encoded viral protein to minimize the potential effect on the function of the viral protein. Conservative amino acid substitutions are well understood in the art (e.g. BLOSUM substitution matrices) and the codons encoding such conservative amino acid substitutions may be readily derived from the genetic code.

Alternatively, or in addition to, the elimination of PAM sequences phage genome to evade Cas9 surveillance and inactivation, the phage may encode one or more proteins identified as inhibitors of Cas9 ("anti-Cas9 proteins") including but not limited to the *Listeria monocytogenes* ACRIIA2 and AcrIIA4 proteins (Rauch, et al (2017) Cell 168:1-2:150-158) and the anti-CRISPR proteins of *Neisseria meningitides* (Pawluk, et al (2016) 167(7):1829-1838). Expression of the anti-Cas9 protein in the bacterial host cell diminishes the ability of the host cell to neutralize the engineered phage of the present invention. The generation of nucleic acid sequences encoding anti-Cas9 proteins, incorporation of such sequences into the phage genome to achieve expression of the anti-Cas9 protein in the bacterial target cell may be achieved in substantial accordance with the methods previously discussed hereinabove with respect to the expression of mAPCC proteins.

PEGylation of Bacteriophage:

A wide variety of chemistries may be employed for the PEGylation of phage. The PEG molecules useful in the practice of the present invention have an average molecular weight of from about 500 to about 100,000 daltons, more typically from about 1000 to about 20,000 daltons, or from about 5,000 to about 10,000 daltons.

PEGylation of bacteriophage may be accomplished in substantial accordance with techniques well known in the art such as those prepared in substantial accordance with the teaching of Carlton, et al U.S. Pat. No. 7,332,307 B2 issued Feb. 19, 2008, the entire teaching of which is herein incorporated by reference. The most common chemistry employed for the PEGylation of biologics proceeds through the linkage of PEG to the epsilon amino group of surface lysine residues through the use of an NHS activated PEG ester. Excess PEG and NHS is typically removed by convention techniques such as differential centrifugation, dialysis or chromatographic techniques.

The PEGylation of various agents for systemic administration has indicated that there is an optimal range of the ratio of PEG molecules to the agent to preserve efficacy while provide immune evasion. Extensive PEGylation of the bacteriophage may provide additional protection from immune surveillance (typical quantified by serum half-life) but at the expense of infectivity of the target cell species. Striking the optimal balance of these competing factors will vary with respect to the composition to be administered and the particular clinical need to be addressed by the composition. However, the determination of the degree of range of PEGylation (both with respect to the ratio of PEG molecules to phage and the optimal molecular weight PEG to be employed) may be readily determined by the skilled artisan using conventional in vitro testing to identify the parameters of infectivity relative to the degree of PEGylation and animal studies to evaluate the immune evasion (e.g. serum half-life) relative to the degree of PEGylation. The particular balance of these factors will depend on the particular application for which the engineered phage is being designed. However, the degree of PEGylation may be controlled by the variation of reaction parameters such as concentration and incubation time and the nature of the PEG to be employed controlled by the selection of reactants. Kim, et al. (Microbial Biotechnology (2008) 1(3):247-25) exemplify methods for varying and quantifying the degree of PEGylation of bacteriophage identifying ratios of bacteriophage to PEG that resulted in PEGylated bacteriophage retaining infectivity of the target cell while providing increased serum half-life. While these studies were conducted with *Listeria* phageA511 and *Salmonella* phage Felix-01, the optimal degree of PEGylation identified is informative of the relative degrees of PEGylation of phage in other applications and the methodology employed to determine the optimal parameter may be readily employed by the skilled artisan with respect other phages.

Methods of Use:

The compositions of the present invention described herein are useful in the treatment of infectious diseases in mammalian subjects. Infectious diseases are those disease states caused by the presence of a pathogenic bacteria. The compositions of the present invention are useful in the treatment of a disease states arising from infections from a potentially any bacterial species for which a bacteriophage exists. Examples of particular bacterial infections amenable to treatment with the compositions of the present invention include but are not limited to *Escherichia coli*, *Staphylococcus* species including *Staphylococcus aureus*, including methicillin resistant or multidrug resistant *S. aureus*; *Streptococcus* species including *Streptococcus pneumoniae*, *Streptococcus agalactiae*, *Streptococcus pyrogenes*, *Propionibacterium acne*, *Candida albicans*, *Helicobacter pylori*, *Mycobacterium tuberculosis*, and *Haemophilus influenza*.

As used herein the term "mammalian subject" refers to an individual of a variety of mammalian species including not limited to humans, pigs, horses, cattle, dogs, and cats. Due to the selective nature of the bacteriophage, the recombinant PEGylated bacteriophages of the present invention are typically administered to a mammalian subject in need of treatment following diagnosis and identification of the bacterial species causative of the infection in the subject and the administration of an engineered phage of the present invention infectious to said bacterial species. The diagnosis of the causative agent of bacterial infections is within the skill of the ordinary clinician using routine clinical testing procedures. Consequently, the compositions of the present invention provide the opportunity to selectively eliminate bacterial infections. The compositions or the present invention may be provided in dosage regimens permitting multiple rounds of administration.

In some instances, it may be desirable to administer a combination of compositions of the present invention having tropism for various bacterial species. For example, in situations where time or circumstances do not permit characterization of the source of the bacterial infection it may be useful to administer a cocktail of the compositions of the present invention directed against different bacterial strains or subtypes. Consequently, the present invention provides for the contemporaneous administration of multiple types of phage to provide multi-pronged attack on multiple bacterial species may be achieved by the simultaneous, contemporaneous, or sequential administration of a combination of the recombinant PEGylated bacteriophages of the present invention the combination containing phages specific for multiple bacterial targets.

The recombinant PEGylated bacteriophages of the present invention may be administered to a mammalian subject by a variety of routes of administration including local administration (e.g. intratumoral injection), regional administration (e.g. intraperitoneal, intravesicular, or intrahepatic arterially) and systemic administration (e.g. intramuscular and intravenous).

The recombinant PEGylated bacteriophages of the present invention may optionally be administered in simultaneous, contemporaneous, or sequential combination with antibiotic compounds. Classes of antibiotic compounds useful in combination with the compositions of the present invention include penicillins, cephalosporins, polymyxins, rifamycins, quinolones, sulfonamides, macrolides, lincosamides, tetracyclines and bacterial aminoglycosides.

The recombinant PEGylated bacteriophages of the present invention may also be administered in simultaneous, contemporaneous, or sequential combination with one or more compositions that aid in the recruitment and maturation of antigen presenting cells including but not limited to IL-4, GM-CSF, CD40 ligand, TNF-alpha or LPS.
Immunotherapy:

The compositions of the present invention are also useful recruiting the mammalian immune system to generate and anti-bacterial response and optionally providing a durable immune response to the bacteria species. The compositions of the present invention result in the expression of an mAPCC at one or more sites of infection causing the recruitment of APCs to the infection site where such APCs are presented with a highly enriched population of molecules derived from the pathogenic bacteria which are taken up by the APCs and presented to T-cells resulting in the generation of memory B-cells expressing antibodies specific against these pathogenic bacterial molecules to aid in the eradication of the pathogenic bacteria from the mammalian subject as well as immunizing the mammalian subject against future infection by said pathogenic bacteria species and potentially against other bacteria possessing cross-reactive antigens. The degree of immunization achieved may readily be determined by the presence and prevalence of circulating neutralizing antibodies against the bacterial target using conventional laboratory techniques. It is not necessary for the mammalian subject to demonstrate seroconversion against the bacterial target to achieve a durable immune response against future infection.
Formulations For administration to a mammalian subject, the a therapeutically effective amount of engineered PEGylated phage of the present invention is provided in a pharmaceutically acceptable formulation providing one or more pharmaceutically acceptable carriers. The term "pharmaceutically acceptable" refers to molecular entities and compositions that do not produce an allergic or similar untoward reaction when administered to a human. Examples of pharmaceutically acceptable carriers includes water, solvents, dispersion media, coatings, antibacterial and antifungal agents, ethanol, glycerol, propylene glycol, surfactants. When the agent is formulated as a solution or suspension, the agent is typically provided in an acceptable carrier, preferably an aqueous carrier. A variety of aqueous carriers may be used, e.g., water, buffered water, 0.8% saline, 0.3% glycine, hyaluronic acid and the like. The formulations may further provide isotonic agents such as sugars or sodium chloride. The pharmaceutical formulations of the present invention may be sterilized by conventional, well known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan, monolaurate, triethanolamine oleate, etc.

The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

Therapeutically effective amount refers to a quantity of phage administered sufficient to result in substantial bacteriolysis or bacteriostasis of the target bacteria in response to the administration of a recombinant PEGylated phage of the present invention. For systemic administration to a mammalian subject, the PEGylated phage of the present invention is administered systemically at a dosage of from about $1 \times 10^9$ to about $1 \times 10^{13}$ pfu/kg, alternatively from about $1 \times 10^{10}$ to about $1 \times 10^{12}$ pfu/kg of bodyweight. In more local administration, In one embodiment, the PEGylated phage is lyophilized and packaged and reconstituted with a pharmaceutically acceptable solution contemporaneous with the time of administration.

In one embodiment of the invention, the formulations are prepared as injectables, either as liquid solutions or suspensions; solid forms suitable for solution in, or suspension in, liquid prior to injection can also be prepared. The formulation can also be emulsified. Sterile injectable solutions are prepared by incorporating the active compounds in the required amount in the appropriate solvent with various of the other ingredients enumerated above, as required, followed by filtered sterilization.

The present invention further provides pharmaceutically acceptable formulations of the engineered phage of the present invention are prepared for topical administration. Such formulations are particularly adapted for the treatment of infection at wound sites. The compositions of the invention can also be administered in topical formulations or polymer matrices, hydrogel matrices, polymer implants, or encapsulated formulations to allow slow or sustained release of the compositions. Such formulations may also contain additional antibiotic agents such as erythromycin, clindamycin, gentamycin, tetracyclines, or other antibiotics typically formulated for topical administration.

The compositions of the present invention further provide pharmaceutically acceptable formulations for administration by inhalation either through liquid mists or dry powder inhalers useful for the administration of lyophilized phage of the present invention.

The formulations of the present invention, may optionally contain one or more compositions that aid in the recruitment and maturation of antigen presenting cells including but not limited to IL-4, GM-CSF, CD40 ligand, TNF-alpha or LPS.

Kits:

The compositions of the present invention may be provided in kits providing a companion diagnostic to monitor for the presence of the targeted pathogenic bacteria and instructions for use. In one embodiment of the invention, a pharmaceutically acceptable formulation comprising the bacteriophage of the present invention is provided in a kit along a companion diagnostic to identify the presence of neutralizing antibodies against the targeted pathogenic bacteria and instructions for use.

We claim:

1. A recombinantly modified PEGylated bacteriophage, said PEGylated bacteriophage capable of infecting a bacterial cell, the genome of said bacteriophage comprising an expression cassette comprising a promoter active in said bacterial cell operably linked to a nucleic acid sequence encoding an mAPCC polypeptide, said expression cassette inserted into a non-essential region of said bacteriophage genome, such that infection of a bacterial cell by said recombinantly modified bacteriophage results in the expression of said mAPCC polypeptide in said infected bacterial cell, said bacteriophage further comprising modifications to the bacteriophage genome to eliminate at least one protospacer adjacent motif, and wherein said bacteriophage further comprises an expression cassette comprising a promoter active in said bacterial cell operably linked to a nucleic acid sequence encoding an anti-Cas9 protein, said anti-Cas9 protein selected from the Listeria monocytogenes ACRIIA2 and AcrIIA4 anti-Cas9 proteins or the anti-CRISPR proteins of Neisseria meningitides AcrIIC1$_{Nme}$, AcrIIC2$_{Nme}$ or AcrIIC3$_{Nme}$, said expression cassette inserted into a non-essential region of said bacteriophage genome, such that infection of a bacterial cell by said recombinantly modified bacteriophage results in the expression of said anti-Cas protein in said infected bacterial cell.

2. The recombinantly modified PEGylated bacteriophage of claim 1 wherein said bacteriophage is a lytic bacteriophage.

3. The recombinantly modified PEGylated bacteriophage of claim 1 wherein said mAPCC polypeptide is selected from the group consisting of fMLP, MCP-1, MCP-2, MCP-3, MIP-1 α/LD78, MIP-1 β, MIP-3 α, MIP-3β, 6-CKINE, lymphotactin and RANTES.

4. A method of inducing lysis of a bacterial cell and expression of a mAPCC molecule in said bacterial cell by contacting said bacterial cell with a recombinantly modified PEGylated lytic bacteriophage of claim 1, said PEGylated bacteriophage capable of infecting and inducing the lytic pathway of said bacterial cell, the genome of said bacteriophage comprising an expression cassette comprising a promoter active in said bacterial cell operably linked to a nucleic acid sequence encoding an mAPCC polypeptide, said expression cassette inserted into a non-essential region of said bacteriophage genome, such that infection of a bacterial cell by said recombinantly modified bacteriophage results in the expression of said mAPCC polypeptide in said infected bacterial cell and lysis of said bacterial cell.

5. The method of claim 4 wherein the recombinantly modified PEGylated bacteriophage of claim 1, said bacteriophage further comprises an expression cassette comprising a promoter active in said bacterial cell operably linked to a nucleic acid sequence encoding an anti-Cas9 protein, said expression cassette inserted into a non-essential region of said bacteriophage genome, such that infection of a bacterial cell by said recombinantly modified bacteriophage results in the expression of said anti-Cas protein in said infected bacterial cell.

6. The method of claim 4 wherein said bacterial cell is present in a mammalian subject.

7. The method of claim 6 wherein said mammalian subject is selected from the group consisting of human, dogs, cats, cattle and horses.

8. The method of claim 6 wherein said bacteriophage is administered at a dosage of from $1 \times 10^9$ to about $1 \times 10^{13}$ pfu/kg of bodyweight of said mammalian subject.

9. A pharmaceutically acceptable formulation of a recombinantly modified PEGylated bacteriophage, said PEGylated bacteriophage capable of infecting a bacterial cell, the genome of said bacteriophage comprising an expression cassette comprising a promoter active in said bacterial cell operably linked to a nucleic acid sequence encoding an mAPCC polypeptide, said expression cassette inserted into a non-essential region of said bacteriophage genome, such that infection of a bacterial cell by said recombinantly modified bacteriophage results in the expression of said mAPCC polypeptide in said infected bacterial cell, wherein said recombinantly modified PEGylated bacteriophage further comprises modifications to the bacteriophage genome to eliminate at least one protospacer adjacent motif, and wherein said recombinantly modified PEGylated bacteriophage further comprises an expression cassette comprising a promoter active in said bacterial cell capable operably linked to a nucleic acid sequence encoding an anti-Cas9 protein, said anti-Cas9 protein selected from the Listeria monocytogenes ACRIIA2 and AcrIIA4 anti-Cas9 proteins or the anti-CRISPR proteins of Neisseria meningitides AcrIIC1$_{Nme}$, AcrIIC2$_{Nme}$ or AcrIIC3$_{Nme}$, said expression cassette inserted into a non-essential region of said bacteriophage genome, such that infection of a bacterial cell by said recombinantly modified bacteriophage results in the expression of said anti-Cas protein in said infected bacterial cell.

* * * * *